(12) United States Patent
Zhang et al.

(10) Patent No.: US 10,765,967 B2
(45) Date of Patent: Sep. 8, 2020

(54) PROCESS FOR PURIFYING NADPH

(71) Applicants: BONTAC BIO-ENGINEERING(SHENZHEN) CO.,LTD, Shenzhen (CN); JIANGXI BONTAC GREEN-BIOCATALYSIS ECOINDUSTRIAL PARK CO.,LTD, Nanchang (CN)

(72) Inventors: Qi Zhang, Shenzhen (CN); Dongmin Zhang, Shenzhen (CN); Rongzhao Fu, Shenzhen (CN)

(73) Assignees: BONTAC BIO-ENGINEERING (SHENZHEN) CO., LTD, Shenzhen (CN); JIANGXI BONTAC GREEN-BIOCATALYSIS ECOINDUSTRIAL PARK CO., LTD., Nanchang (CN)

( * ) Notice: Subject to any disclaimer, the term of this patent is extended or adjusted under 35 U.S.C. 154(b) by 438 days.

(21) Appl. No.: 15/575,389

(22) PCT Filed: Dec. 14, 2016

(86) PCT No.: PCT/CN2016/109849
§ 371 (c)(1),
(2) Date: Nov. 20, 2017

(87) PCT Pub. No.: WO2018/107377
PCT Pub. Date: Jun. 21, 2018

(65) Prior Publication Data
US 2019/0336887 A1 Nov. 7, 2019

(51) Int. Cl.
*B01D 15/32* (2006.01)
*B01D 15/36* (2006.01)
*B01D 61/02* (2006.01)
*B01D 61/14* (2006.01)
*B01D 63/02* (2006.01)
*C07H 19/207* (2006.01)

(52) U.S. Cl.
CPC ......... *B01D 15/363* (2013.01); *B01D 61/027* (2013.01); *B01D 61/145* (2013.01); *B01D 61/147* (2013.01); *B01D 63/02* (2013.01); *C07H 19/207* (2013.01); *B01D 15/327* (2013.01)

(58) Field of Classification Search
CPC .. B01D 15/363; B01D 15/327; B01D 61/027; B01D 61/145; B01D 61/147; B01D 63/02; C07H 19/16; C07H 19/207; C07H 1/06; C07H 19/1207
See application file for complete search history.

(56) References Cited

U.S. PATENT DOCUMENTS 3,749,709 A 7/1973 Nelboeck-Hochstetter et al.

FOREIGN PATENT DOCUMENTS

| CN | 103233051 A | 8/2013 |
|---|---|---|
| CN | 104876993 A | 9/2015 |
| CN | 104876994 A | 9/2015 |
| CN | 104892710 A | 9/2015 |

OTHER PUBLICATIONS

CN 103233051 machine translation Mar. 27, 2020.*
Markham, K. A. et al, Analytical Procedures for the Preparation, Isolation, Analysis and Preservation of Reduced Nicotinamides Current Analytical Chemistry, Dec. 31, 2016, Issue No. 4, vol. 2.

* cited by examiner

*Primary Examiner* — Benjamin L Lebron
(74) *Attorney, Agent, or Firm* — Bayramoglu Law Offices LLC

(57) ABSTRACT

The present invention relates to a process for purifying crude NADPH product prepared by biocatalysis. The objective of the present invention is to solve the technical problems of low yield and low purity of the purified product in the existing ion exchange resin method. The present invention comprises sequentially the following steps: pretreatment, loading onto an ion column, elution of cations, pre-elution of impurities etc. The yield of the purification process disclosed in the present invention can be up to 85% or higher and the purified NADPH has a purity of up to 98% or higher.

17 Claims, No Drawings

PROCESS FOR PURIFYING NADPH

CROSS REFERENCE TO RELATED APPLICATIONS

This application is the national phase entry of International Application No. PCT/CN2016/109849, filed on Dec. 14, 2016, the entire content of which is incorporated herein by reference.

TECHNICAL FIELD

The present invention relates to the technical field of purification of nucleotide coenzymes, and more particularly to a process for purifying crude NADPH product prepared by biocatalysis.

BACKGROUND OF THE INVENTION

NADPH is an abbreviation of reduced form of nicotinamide adenine dinucleotide phosphate, which is a very important physiological substance present in all kinds of living cells, including human cells, and a co-factor for a number of enzymes that catalyze the oxidation-reduction reactions, and is referred to as reduced coenzyme II.

NADPH is involved in a variety of anabolic reactions, such as the lipid, fatty acid and nucleotide synthesis, in the living cells, in which NADPH is needed as a reducing agent and a hydrogen donor. In addition, NADPH not only serves as a carrier for hydrogen transfer, but also as a mediator for phosphoryl transfer and participates in a variety of synthetic reactions. Today, NADPH is widely used in the production of various kinds of products in pharmaceutical and biochemical enterprises. With the intensive study on NADPH in the area of treatment and prevention of diseases, NADPH becomes increasingly important as a health care product, and the market demand grows year by year.

At present, the methods for preparing NADPH mainly include 1. yeast fermentation; 2. chemical synthesis; and 3. biocatalysis. Chemical synthesis has the disadvantages of high cost and production of chiral compounds. The NADPH produced by yeast fermentation contains some organic solvent residue. Biocatalysis is the most environmentally-friendly pollution-free method for preparing NADPH, because no organic solvent residue and no problem of chirality are present and the prepared NADPH is an isoform of that existing in an organism.

In an existing method for preparing NADPH by biocatalysis, NADP is used as a substrate for preparing NADPH in the presence of a dehydrogenase. The crude NADPH product prepared through the method needs to be further purified to obtain a pure NADPH product. The purification methods commonly used at present include liquid chromatography and ion exchange resin method. Liquid chromatography has the advantages of high purity and high yield of the purified product. However, since NADPH has a functional group with strong polarity and hydrophilicity, an ion-pairing agent and a buffer salt are introduced in the process of purification by liquid chromatography. The ion-pairing agent is difficult to separate, and the use of an organic reagent is needed during the purification process, so liquid chromatography brings new impurities and has a high cost, and is thus not suitable for use in industrial production. By means of the ion exchange resin method generally used in the industry at present, the purity of NADPH obtained is only about 95% at most, and the yield is only about 60% at most. Therefore, the production capacity is greatly limited and cannot meet the market demand.

SUMMARY OF THE INVENTION

In view of the disadvantages in the prior art, an object of the present invention is to provide a novel ion exchange resin method for purifying crude NADPH products prepared by biocatalysis, which has the advantages of high yield and high purity of the product, so as to solve the technical problems of low yield and low purity of the purified product in the existing ion exchange resin method.

To achieve the above object, the present invention provides a process for purifying NADPH. The process comprises sequentially the following steps.

A. Pretreatment: A crude NADPH product prepared by biocatalysis is filtered through a microfiltration membrane that is a hollow fiber membrane having a pore size of 0.1-0.5 µm.

The process for purifying NADPH provided in the present invention is suitable for the treatment of crude NADPH products obtained through the preparation of NADPH by biocatalysis. The biocatalysis is specifically a method in which a substrate is catalytically converted into NADPH in the presence of a biological enzyme, where the biological enzyme is a dehydrogenase or a combination of a dehydrogenase with one or more other enzymes; the substrate may be NADP or a precursor able to be converted into NADP; and the so-called crude NADPH product refers to an enzymatic reaction solution without any treatment obtained after the substrate is enzymatically reacted completely. The microorganisms and the solid catalyst existing in the reaction process will affect the purity and the yield of the purification process, so NADPH is primarily purified by a microfiltration membrane, to remove the solid particles and the microorganisms existing in the reaction process. If the pore size of the membrane selected is too large, some solid or microorganisms cannot be removed; and if the pore size of the membrane is too small, NADPH cannot penetrate through.

B. Loading onto an ion column: The microfiltered crude NADPH product obtained in Step A is loaded onto an anion exchange resin column.

The crude NADPH product is loaded onto an anion exchange resin column, mainly for the purpose of adsorbing NADPH onto the ion exchange resin by ionic bonding, and then eluting off the impurities and NADPH respectively under different eluting conditions, to obtain a pure product.

C. Elution of cations: After loading, the ion column is washed with purified water until no cations are contained in the eluate.

The crude NADPH product contains metal ions and organic cations. The cations themselves are uneasy to be adsorbed by the anion exchange resin; however, affinity adsorption of the cations is prone to occur after NADPH is adsorbed to the anion exchange resin, which causes the low content and purity of the product, if the cations are not eluted off.

D. Pre-elution of impurities: The ion column is washed with a 0.07-0.5 mol/L sodium chloride solution until no substances having UV absorption at 260 nm are contained in the eluate.

The crude NADPH product contains impurities including the raw material and some reaction by-products. These impurities have different point charges. According to the different point charges, weakly ionic impurities can be eluted off with a low concentration of sodium chloride solution. During use, the concentration of the sodium chloride solution is suitably not too high, because if the concentration is too high, NADPH would be eluted off, causing a decreased yield. The concentration of the sodium chloride solution is suitably not too low either, because if the concentration is too low, the weakly ionic impurities cannot be eluted off, leading to a low and unsatisfactory purity of NADPH. Both NADPH and the impurities have UV absorption at 260 nm, so the detection wavelength is selected to be 260 nm.

E. Elution of product: The ion column is washed with an aqueous solution containing 0.5 mol/L sodium chloride and 7% (V/V %) ethanol, and the eluate having UV absorption at 340 nm is collected.

The eluent for the product is 0.5 mol/L sodium chloride and 7% (V/V %) ethanol in water. If the elution conditions are lowered, tailing or incomplete elution of the product is caused, resulting in a too low yield of the product. If the concentration of sodium chloride or ethanol is further increased, some of the strongly ionic impurities will be eluted off into the product, causing reduced purity. The product has UV absorption at 340 nm, and the impurities do not. Therefore, the product is collected at 340 nm.

F. The climate obtained in Step E is concentrated and dried, to obtain a purified NADPH product.

Preferably, the anion exchange resin is a macroporous styrenic quaternary ammonium type I strong basic anion exchange resin. It is found by the present inventors after experimentally screening of a large number of anion exchange resins that the macroporous styrenic quaternary ammonium type I strong basic anion exchange resin has a high loading capacity for NADPH. When the resin is used in the purification process, the yield of the product NADPH obtained is high, the purity can be up to 98% or higher, and the practical process operations and the resin regeneration process are also relatively simple.

More preferably, the loading amount of the crude NADPH product is 9-15 g of NADPH per g of the macroporous styrenic quaternary ammonium type I strong basic anion exchange resin.

When the crude NADPH product has a low pH, the process preferably further comprises: adjusting the crude NADPH product to pH 8.0-11.0, to maintain the product to be stable, before Step A. More preferably, the crude NADPH product is adjusted to pH 9.0-10.0.

Since NADPH is more stable in a basic environment, preferably, the process further comprises a step of pretreating the anion exchange resin by soaking the anion exchange resin in a sodium hydroxide solution to convert the resin from Cl$^-$ type to OH$^-$ type, and then washing with purified water to nearly neutral. The concentration of the sodium hydroxide solution is preferably 0.1-0.5 mol/L.

To allow the anion exchange resin to be used cyclically and reduce the production cost, it is preferable that the process further comprises the step of regenerating the anion exchange resin, where the regeneration solution used during regeneration is an aqueous solution containing 1.0 mol/L sodium chloride and 0.1 mol/L hydrochloric acid, the washing rate is 0.8-1.5 BV/H, and the amount of the regeneration solution used is 2.0 BV. After regeneration, the resin is flushed with purified water to nearly neutral.

Preferably, Steps C and D are under full detection by a nucleic acid protein detector in the purification process, and the eluate is collected when the reading of the nucleic acid protein detector starts to rise, and the collection is terminated when the reading starts to decline.

In the purification process, the concentration in Step E may be carried out by any suitable means of concentration known in the art. Preferably, the concentration treatment comprises microfiltration, ultrafiltration, and nanofiltration. The content of the product in the solution collected after purification is low, and a large amount of water, salts, and ethanol are contained. Salts and ethanol can be removed and an effect of concentration can be achieved by nanofiltration. A hollow fiber membrane having a pore size of 0.1-0.5 μm can be used for the microfiltration, to remove the solid particles and some microorganisms. An ultrafiltration membrane with a molecular weight cutoff of 10 K can be used for the ultrafiltration, to remove endotoxins and microorganisms. A spiral-wound membrane with a molecular weight cutoff of 100-400 can be used for the nanofiltration, to remove small molecule impurities.

In the purification process, the drying in Step F may be carried out by any suitable means of drying known in the art. Preferably, the drying is vacuum freeze-drying.

Beneficial Effect:

Compared with the prior art, the process for purifying NADPH provided in the present invention has the advantages of high yield and high purity of the purified product. If is confirmed by industrial practice that the yield of the purification process can be up to 85% or higher and the purified NADPH has a purity of up to 98% or higher. Moreover, the process is green and environmentally friendly because no toxic and harmful organic solvent is used, the process is simple and convenient for operation, and the production cost is low, such that the purified product is highly competitive in the market. This process has universal applicability to the purification of crude NADPH products obtained from biocatalytic preparation of NADPH.

DETAILED DESCRIPTION OF THE INVENTION

The present invention will be described in further detail with reference to specific examples. The following examples are illustrative of the present invention and the present invention is not limited thereto.

EXAMPLE 1

Object treated: four batches of crude NADPH product solutions biocatalytically prepared by Bontac Bio-engineering (Shenzhen) Co., Ltd (where NADP is used as a substrate for preparing NADPH in the presence of a dehydrogenase). The NADPH content in the four batches of crude NADPH product solutions is shown in Table 1.

The process for purifying the four batches of crude NADPH product solutions was as follows.

1. Pretreatment of resin: A macroporous styrenic quaternary ammonium type I strong basic anion exchange resin was packed in an ion column, soaked by adding a 0.1-0.5 mol/L sodium hydroxide solution, and then washed with purified water to nearly neutral.

2. Pretreatment of crude NADPH product: The biocatalytically prepared crude NADPH product was adjusted to pH 9.0-10.0, and then microfiltered through a hollow fiber membrane having a pore size of 0.45 μm.

3. Loading onto ion column: The microfiltered crude NADPH product obtained in Step 2 was loaded onto the ion column pretreated in Step 1 at a loading rate of 0.8-1.5 BV/H in a loading amount of 9-15 g/g anion exchange resin.

4. Elution of cations: After loading, the ion column was washed with purified water at a washing rate of 0.5-2.0

BV/H. The eluate was detected on line by a water hardness indicator throughout the whole process, and the washing was stopped until the color of the water hardness indicator did not change (where the water hardness indicator changing from blue to red indicates that the cations are completely removed, and the water hardness indicator remaining blue without change indicates that no high-valency cations exist).

5. Pre-elution of impurities: The ion column was washed with a 0.3 mol/L sodium chloride solution. The eluate was detected on line by a nucleic acid protein detector at 260 nm throughout the whole process. The changes in the reading of the nucleic acid protein detector were carefully observed, the reading initially rose and then declined, and the washing was stopped when the reading did not change any longer.

6. Elution of product: The ion column was washed with an aqueous solution containing 0.5mol/L sodium chloride and 7% (V/V %) ethanol. The eluate was detected on line by a nucleic acid protein detector at 340 nm throughout the whole process. The changes in the reading of the nucleic acid protein detector were carefully observed. The eluate was collected when the reading started to rise, and the collection was terminated when the reading started to decline. After the eluate was collected, the ion column was regenerated.

7. Post-treatment: The dilate collected in Step 6 was subjected to microfiltration, ultrafiltration, and nanofiltration sequentially, and dried in a vacuum freeze-drier after being concentrated to 100-150 g/L, to obtain a NADPH product. During the microfiltration process, a hollow fiber membrane with a pore size of 0.45 μm was used; during the ultrafiltration process, an ultrafiltration membrane with a molecular weight cutoff of 10 K was used; and during the nanofiltration process, a spiral wound membrane with a molecular weight cutoff of 10 100-400 was used.

The content and purity of the NADPH products obtained after purification of the four batches were determined by high performance liquid chromatography (HPLC), and the yield was calculated. The results are shown in Table 1.

TABLE 1

| Batch | Crude NADPH product solution | | Purified NADPH product | | | |
|---|---|---|---|---|---|---|
| | Loading volume/L | NADPH content/g | NADPH content/g | Enzyme activity/% | Purity/% | Yield/% |
| 1 | 13000 | 10289 | 8879.4 | 98.3 | 98.7 | 86.3 |
| 2 | 15000 | 12006 | 10469.2 | 98.1 | 98.5 | 87.2 |
| 3 | 36000 | 23069 | 20000.8 | 98.2 | 98.4 | 86.7 |
| 4 | 38000 | 25736 | 22081.5 | 98.5 | 99.1 | 85.8 |

EXAMPLE 2

The ion column was regenerated as follows.

1. Flushing: The by-products remaining in the resin were flushed out with a large amount of purified water, until the reading of the nucleic acid protein detector dropped to 0.5 or below.

2. Regeneration: An aqueous solution containing 1.0 mol/L sodium chloride and 0.1 mol/L hydrochloric acid was formulated and used as a regeneration solution. The regeneration valve was opened, the regeneration pump was started, and the ion column was washed with the regeneration solution in an amount of 2.0 BV at a washing rate of 0.8-1.5 BV/H.

3. Water washing: After being regenerated with the regeneration solution, the ion column was washed with 2-3 column volumes of water to nearly neutral. Then the ion column could be used in next purification with good adsorptivity.

What is claimed is:

1. A process for purifying NADPH, comprising the following steps:
   A. pretreatment: filtering a crude NADPH product prepared by biocatalysis through a microfiltration membrane to obtain a microfiltered crude NADPH product, wherein the microfiltration membrane is a hollow fiber membrane having a pore size of 0.1-0.5 μm;
   B. loading onto an ion column: loading the microfiltered crude NADPH product obtained in Step A onto an anion exchange resin column;
   C. elution of cations: after loading, washing the ion column with purified water until no cations are contained in the eluate;
   D. pre-elution of impurities: washing the ion column with a 0.07-0.5 mol/L sodium chloride solution until no substances having UV absorption at 260 nm are contained in the eluate;
   E. elution of product: washing the ion column with an aqueous solution containing 0.5 mol/L sodium chloride and 7% (V/V) ethanol, and collecting an eluate having UV absorption at 340 nm; and
   F. concentrating and drying the eluate obtained in Step E to obtain a purified NADPH product.

2. The process for purifying NADPH according to claim 1, wherein the anion exchange resin is a macroporous styrenic quaternary ammonium type I strong basic anion exchange resin.

3. The process for purifying NADPH according to claim 2, wherein the crude NADPH product is loaded in an amount of 9-15 g of NADPH per g of the anion exchange resin.

4. The process for purifying NADPH according to claim 1, wherein the process further comprises adjusting the crude NADPH product to pH 8.0-11.0 before Step A when the crude NADPH product has a pH less than 8.0-11.0.

5. The process for purifying NADPH according to claim 4, wherein the process further comprises adjusting the crude NADPH product to pH 9.0-10.0 before Step A when the crude NADPH product has a pH less than 9.0-10.0.

6. The process for purifying NADPH according to claim 1, wherein the process further comprises a step of pretreating the anion exchange resin by soaking the anion exchange resin with a sodium hydroxide solution and washing with purified water.

7. The process for purifying NADPH according to claim 1, wherein the process further comprises a step of regenerating the anion exchange resin, wherein a regeneration solution used during regeneration is an aqueous solution comprising 1.0 mol/L sodium chloride and 0.1 mol/L hydrochloric acid, wherein a washing rate of the regeneration is 0.8-1.5 BV/H, and an amount of the regeneration solution used is 2.0 BV; wherein the resin is flushed with purified water after regeneration.

8. The process for purifying NADPH according to claim 1, wherein Steps C and D are under detection by a nucleic acid protein detector, wherein the eluate is collected when a reading of the nucleic acid protein detector starts to rise, and the collection is terminated when the reading starts to decline.

9. The process for purifying NADPH according to claim 1, wherein the concentrating of step F comprises microfiltration, ultrafiltration, and nanofiltration sequentially, wherein a hollow fiber membrane having a pore size of 0.1-0.5 μm is used for the microfiltration, an ultrafiltration membrane with a molecular weight cutoff of 10 K is used for the ultrafiltration, and a spiral wound membrane with a molecular weight cutoff of 100-400 is used for the nanofiltration.

10. The process for purifying NADPH according to claim 1, wherein the drying of step F is a vacuum freeze-drying.

11. The process for purifying NADPH according to claim 2, wherein the process further comprises adjusting the crude NADPH product to pH 8.0-11.0 before Step A when the crude NADPH product has a pH less than 8.0-11.0.

12. The process for purifying NADPH according to claim 11, wherein the process further comprises adjusting the crude NADPH product to pH 9.0-10.0 before Step A when the crude NADPH product has a pH less than 9.0-10.0.

13. The process for purifying NADPH according to claim 2, wherein the anion exchange resin is conducted with a pretreatment of soaking with a sodium hydroxide solution and washing with purified water.

14. The process for purifying NADPH according to claim 2, wherein the anion exchange resin is conducted with a regeneration, wherein a regeneration solution used during regeneration is an aqueous solution comprising 1.0 mol/L sodium chloride and 0.1 mol/L hydrochloric acid, wherein a washing rate of the regeneration is 0.8-1.5 BV/H, and an amount of the regeneration solution used is 2.0 BV; wherein the resin is flushed with purified water after regeneration.

15. The process for purifying NADPH according to claim 2, wherein Steps C and D are under detection by a nucleic acid protein detector, wherein the eluate is collected when a reading of the nucleic acid protein detector starts to rise, and the collection is terminated when the reading starts to decline.

16. The process for purifying NADPH according to claim 2, wherein the concentrating of step F comprises microfiltration, ultrafiltration, and nanofiltration sequentially, wherein a hollow fiber membrane having a pore size of 0.1-0.5 μm is used for the microfiltration, an ultrafiltration membrane with a molecular weight cutoff of 10 K is used for the ultrafiltration, and a spiral wound membrane with a molecular weight cutoff of 100-400 is used for the nanofiltration.

17. The process for purifying NADPH according to claim 2, wherein the drying of step F is a vacuum freeze-drying.

* * * * *